United States Patent
Hoff et al.

(10) Patent No.: US 6,528,100 B1
(45) Date of Patent: *Mar. 4, 2003

(54) FEED MASS HAVING A MODIFIED PROTEIN STRUCTURE FOR CARNIVOROUS ANIMALS

(75) Inventors: Kjell Arne Hoff, Sandnes (NO); Fred Hirth Thorsen, Hundvag (NO)

(73) Assignee: Nutreco Aquaculture Research Centre AS (NO)

( * ) Notice: Subject to any disclaimer, the term of this patent is extended or adjusted under 35 U.S.C. 154(b) by 0 days.

This patent is subject to a terminal disclaimer.

(21) Appl. No.: 10/163,165

(22) Filed: Jun. 4, 2002

Related U.S. Application Data

(62) Division of application No. 09/673,003, filed as application No. PCT/NO99/00102 on Mar. 25, 1999, now Pat. No. 6,399,117.

(30) Foreign Application Priority Data

Apr. 8, 1998 (NO) .......................................... 19981616
Mar. 25, 1999 (NO) .......................................... 19991468

(51) Int. Cl.[7] .............................................. A23K 1/165
(52) U.S. Cl. .......................... 426/2; 426/442; 426/657; 426/805
(58) Field of Search .......................... 426/2, 442, 657, 426/805

(56) References Cited

U.S. PATENT DOCUMENTS

| | | | |
|---|---|---|---|
| 4,917,904 A | 4/1990 | Wakameda et al. | 426/7 |
| 5,518,742 A | 5/1996 | Soeda et al. | 426/63 |
| 5,658,605 A | 8/1997 | Soeda et al. | 426/7 |

FOREIGN PATENT DOCUMENTS

| | | | |
|---|---|---|---|
| JP | 58028234 | | 2/1983 |
| JP | 58149645 | | 9/1983 |
| JP | 6209716 | | 8/1994 |
| JP | 6261692 | * | 9/1994 |
| JP | 9028312 | * | 2/1997 |

OTHER PUBLICATIONS

Abstract of: Dep. of Fooed Sci., North Caroina State Univ., Raleigh, NC 27695–7624, USA, "Journal of Muscle Foods", (1995) 125–138.

Abstract of : "Enzymic crosslinking as a tool for food colloid theology control and interfacial stabilization", Trends in Food Science & Technology, (1997) 8 (10) 334–339, 57 ref., ISSN: 0924–2244.

Abstract of: "The role of covalent cross–linking in the texturizing of muscle protein sols", *Dep. of food sci.*, North Carolina State Univ., Raleigh, NC 27695–7624, USA, Journal of Muscle foods (1995) 6, (2) 125–138, 51 ref.

Abstract of: "Modification of food proteins by covalent crosslinking", Dep. of Food Tech., Massey Univ., Palmerston North, New Zealand, *Trends in food Science & Technology*, (1991) 2, (8) 196–200, 44 ref.

Abstract of : "Modification of food proteins by covalent crosslinking", Dep. of Food Tech., Massye Univ. Palserston North, New Zealand, *Trends in Food Science & Technology*, (1991) 2 (8) 196–200, 44 ref.

Abstract of: "The usefulness of transglutaminase for food processing", ACS Symp. Ser. (1996), 637 (Biotechnology for Improved Foods and Flavors), 29–38.

Abstract of : "Enzymic crosslinking as a toold for food colloid rheology control and interfacial stabilization" Trends Food Sci. Technology., (1997), * (10), 334–339.

* cited by examiner

*Primary Examiner*—Chhaya D. Sayala
(74) *Attorney, Agent, or Firm*—Vidas, Arrett & Steinkraus, P.A.

(57) ABSTRACT

A method for producing feed for forming into pellets, the pellets produced by the method to be used to feed carnivorous animals. The addition of the enzyme transglutaminase to a feed mass specifically intended for carnivorous fish will catalyze a reaction between the amino acids glutamine and lysine which form part of the protein chains and the raw material of the proteins of the feed, such that a covalent chemical bond is formed between them, which results in shape permanence in the formed, dried, finished pellets, such that the finished pellets do not lose their shape before time of use.

9 Claims, No Drawings

FEED MASS HAVING A MODIFIED PROTEIN STRUCTURE FOR CARNIVOROUS ANIMALS

This application is a divisional of U.S. application Ser. No. 09/673,003, filed Oct. 6, 2000, now U.S. Pat. No. 6,399,117, which was the National Stage of International Application No. PCT/NO99/00102, filed Mar. 25, 1999.

BACKGROUND OF THE INVENTION

The present invention relates to a method for the modification of protein structure in finish shaped feed pellets, balls or the like, among other reasons in order to contribute to strengthening the permanence of the pellet shape in granular feeds of this sort. The invention also relates to feedstuff manufactured according to this method for the formation of a shape-permanent feed in pellet form.

Many types of animals in breeding, e.g. salmon and trout, are carnivorous (meat-eating). Their natural food consists of insects (for salmon and trout in the freshwater phase), fish and crustaceans. For other carnivorous farmed animals, such as mink and foxes, the feed may also contain the mammalian flesh, for example fresh slaughterhouse waste. Insects and crustaceans have an exoskeleton which i.e. consists of chitin. Chitin is a linear polysaccharide of N-acetyl-D-glucosamine linked by $\beta 1 \rightarrow 4$ bonds. Other structural carbohydrates such as cellulose ($\beta[1 \rightarrow 4]$D-glycose) and alginate (D-mannuronic acid) are not found in these prey animals, nor do they contain starch ($\alpha[1>4]$D-glycose) as energy stores. Nevertheless, salmon, trout and other carnivorous fish and animals have enzymes (for example, amylase) that are capable of breaking down starch in the gut and making it digestible, but they may be less efficient in this respect than herbivorous (plant-eating) fish and animals.

In feeds intended for carnivorous fish it is usual to add between 8% and 25% carbohydrates, for example in the form of wheat or maize, as a binding agent. After pressing, but especially after extrusion, the starch in these carbohydrates will form a matrix or base mass which gives the pellets mechanical strength and shape permanance so that the shape of the pellets can be maintained after drying, further processing, storage and transport.

Carbohydrates are utilised in metabolism as a source of energy. The energy density of carbohydrates is lower than that of protein and fat (17.6; 23.9 and 39.8 MJ/kg respectively). The digestibility of carbohydrates is also lower in carnivorous fish, and declines as the proportion of complex carbohydrates in the feed (above 10%) increases. Experiments have shown that salmonids have no metabolic need for carbohydrates. If fat replaces carbohydrates as an energy source, a carbohydrate-free fish feed of this sort will contain more energy per unit weight, as long as the relative proportions of the other components are held constant.

In order to give feed pellets shape permanence and mechanical strength, as mentioned above, it is known to add a binding agent in the form of 8%–25% carbohydrates, for example wheat and/or maize. After pressing or extrusion in the feedstuff material there will be established a starch matrix of the desired strength.

Other techniques in connection with the forming of feed into pellets balls or the like, have also been described. According to U.S. Pat. No. 4,935,250, for example, a gel or mass of alginate is also produced during the forming.

The patent literature includes descriptions of feeds and feed mixtures in which the mass consists of gelatine or caseinate. See, for example, British Patent No. 2,217,175.

There are also feeds in which the binding characteristics produced by the coagulation of native proteins are exploited; see NO 179 731.

Small feed particles can be produced with the aid of an agglomeration technique, which are based on the principle of aggregating extremely small particles into larger particles. This process does not utilize carbohydrates as a binding agent. The feed components are bound together through various forms of contact bonds between the solid particles in the feed. The different forms of contact bonds can vary from hydrogen bonds, adhesion and cohesion to capillary forces. New covalent bonds are not created in this process. This is an obvious disadvantage for the maintenance of the feed pellet's form and strength, because covalent bonds are stronger than other chemical bonds.

A serious disadvantage of agglomerated feeds is thus that the bonds are weak, and given the lack of a continuous matrix such pellets are friable and fragile. The agglomeration technique cannot be utilised to produce particles of feed in pellet form with a diameter larger than about 2.5–3.0 mm.

In order to be able to produce larger feed particles/fragments/pellets/balls, etc., we must abandon the agglomeration technique without addition of carbohydrate and again return to carbohydrate as a binding agent. In low concentrations, complex carbohydrates such as starch are digested by salmonids, for example, but if their concentration exceeds 10% the digestibility of the carbohydrate fraction decreases (Aksnes A., 1995. Growth, feed efficiency and slaughter quality of salmon, Salmo salar L., given feeds with different ratios of carbohydrate and protein. Aquaculture Nutrition, 1:241–248).

GENERAL DESCRIPTION OF THE INVENTION

The energy content of the carbohydrate fraction may be replaced by fat within the feed recipe. This will result in greater freedom with respect to varying the relative proportions of fat, protein and micronutrients since the carbohydrates make up the remainder of the feed recipe. Such a feed will be richer in energy than an equivalent feed containing carbohydrates, and a reduction in the feed conversion ratio, defined as the quantity of feed consumed to produce one kilo of fish biomass, will be obtained.

In accordance with the present invention one has aimed at showing a method of modifying the protein structure of feeds whose nutrient composition closely resembles the natural choice of foods of carnivorous fish and animals. According to the invention, favourable binding is obtained in feeds—without carbohydrates—resulting in shape permanence in pellets and similar forms of feedstuff, and in such a way that the maximum particle size/pellet diameter can be increased in the case of agglomerated feed while maintaining the shape of the feed. The invention also aims to increase the energy density of all types of feed, particularly fish feeds.

The above-identified objective is reached by proceeding as described herein. A feedstuff that has been treated as described in accordance with this method and which is intended for the forming of pellets or the like, and properties relating thereto are identified herein. Feed pellets made of such a feedstuff, whose protein structure has been modified by the method, are also disclosed herein.

DETAILED DESCRIPTION OF THE PREFERRED EMBODIMENT

The method and product formed by the method thus consists mainly of a feedstuff, or alternatively of one or more of the components of which it consists, for forming pellets, alternatively of coating the surface of the formed pellets, in order to add an enzyme (preferably transglutaminase) that function as a catalyst for the formation of covalent bonds between the amino acids which make up the protein chains in protein raw materials containing proteins in native or denatured form. The raw materials of the protein in the feed mixture include the natural amino acids glutamine and lysine in the protein chains. The added enzyme will act as a catalyst and catalyze the formation of covalent (å-(γ-Glu) Lys) bonds between the amino acids glutamine and lysine in the protein raw ingredients in the feed.

Through the adoption of reaction temperature and reaction time this enzymatic reaction will form a matrix or basic mass of protein raw materials which will exhibit adequate strength to give feed pellets a constant and lasting shape.

In agglomerated feed this enzymatic reaction will lead to covalent transverse bonds (cross-bonds) between the proteins. This will give the agglomerate increased strength by introducing the strongest type of chemical bond in addition to the other three types of chemical bonds which provide the feed product with firmness and strength.

In pressed or extruded feeds, the formation of covalent (å-(γ-Glu)Lys) bonds that lead to the formation of a protein matrix will be able to partially or wholly replace the addition of carbohydrates. This makes it possible to remove carbohydrates from the recipe for the feed, or to reduce the proportion of carbohydrates respectively. Carbohydrates play virtually no part in the natural diet of carnivorous fish and animals, and the total energy density of feed pellets can be increased because both protein and fat are richer in energy than carbohydrates. According to the present invention, an animal feed in the form of pellets will require no other binding agents such as gelling agents in the form of gelatine, for example.

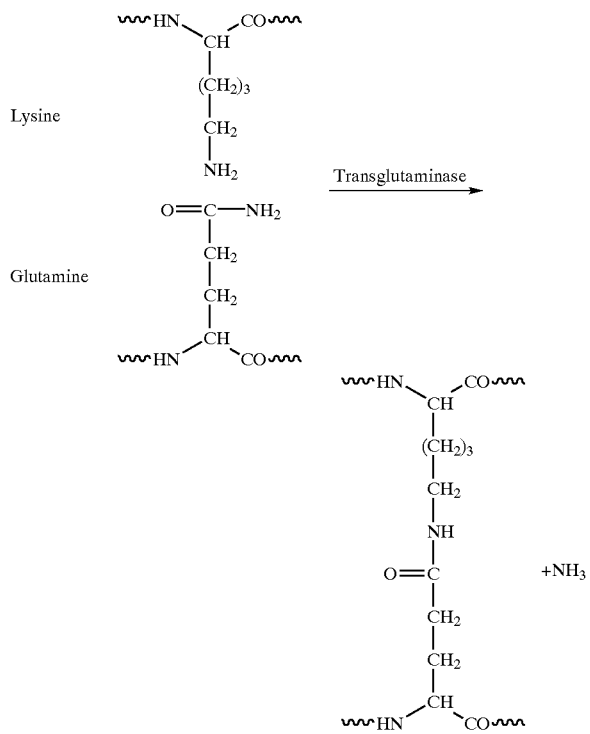

The above reaction formula, in which the enzyme transglutaminase acts as a catalyst, shows the creation of å-(γ-Glutamyl) lysine bond between the amino acids glutamine and lysine.

Transglutaminase is defined as enzymes which are classified as protein-glutamine γ-glutamyltransferase (EC 2.3.2.13; International Union of Biochemistry and Molecular Biology, Nomenclature Committee). Transglutaminase may occur in a pure form or as a distinct premix with suitable filler and transglutaminase in adjusted concentration. Transglutaninase can be added to the other raw ingredients of the feed in the form of a powder, in solution or in suspension.

The term "protein raw materials" refers to raw ingredients that contain protein in either native or denatured form.

Examples include fish meal, stickwater, stickwater concentrate, blood meal, feather meal, bone and horn meal, wheat gluten, maize gluten, soya meal and rapeseed meal. These are only illustrative examples, and do not exclude the use of other raw ingredients in feeds as partial substitutes for or additions to one or more of the said raw ingredients.

The term "feed pellets" refers to particles or fragments, preferably round, which are formed by means of a special process, such that they are of a size and shape that makes them suitable as feed, particularly for carnivorous fish species such as farmed salmon, cod, halibut, sea perch and sea bream.

The activity of the enzyme (transglutaminase) declines at temperatures higher than 50° C., and it is deactivated at temperatures beyond 65° C. The formation of a protein matrix as described here can thus take place under process heat conditions in which the process temperature varies between 0 and 60° C. The shortest process time is obtained at around 50° C., since the process time is lengthened at temperatures above and below this temperature.

Transglutaminase is added to the other ingredients of the feed before these are formed into pellets by a suitable method, since the enzyme can be added as a solution or as a suspension in a suitable liquid, for example water, or blended as a dry ingredient before liquid is added to the mixture. In addition to transglutaminase, an aqueous solution may contain pure water, stickwater or stickwater concentrate, or another protein-rich liquid, for example a non-limiting gelatine solution.

Transglutaminase can also be added to the surface of preformed pellets by a suitable method, in that the enzyme can be added as dissolved in steam, or as a solution, suspension or wash in a suitable liquid such as water.

The fat content of the feed may, according to a non-limiting preferred example, consist of fish-oil, which can be added to the feed either before or after the feed is formed into pellets, or after the pellets have been dried. After the feed has been formed into pellets, the pellets are maintained at a temperature of between 0 and 60° C., so that the transglutaminase enzyme has time to catalyse the å-(γ-Glutamyl) lysine bonds that are desired.

The reaction time is adapted to the reaction temperature.

Finally, the formed pellets are dried to the desired water content/degree of dryness in a suitable dehydration unit, such as a drying cabinet.

The transglutaminase product used in the following examples (from the manufacturer Ajinomoto in Japan) consists of 60% sodium caseinate, 39.5% maltodextrin and 0.5% transglutaminase. A meat grinder with a die size of around 6.5 mm can be used to form the feed into pellets. The apparatus may also comprise an incubator cabinet and a drying cabinet (working temperature about 80–90° C.). In a wear test, a rotation rate of 500 rpm was employed without the use of metal balls.

EXAMPLE 1

500 g fish meal (Norwegian LT meal) and 500 ml water were mixed to formation of a dough which was then formed into pellets with the aid of a meat grinder. The formed pellets were dried for about 35 minutes. 300 g pellets were used for the wear test.

25 g transglutaminase product containing 125 mg transglutaminase and 15 g sodium caseinate was stirred into 500 ml water at about 40° C. The solution was added to 500 g fish meal (Norwegian LT meal), mixed to a dough and formed into pellets with the aid of a meat grinder. These pellets were incubated in the said incubator cabinet for about 60 minutes at about 40° C., and thereafter dried for about 50 minutes. 300 g pellets were used for the wear test.

Result

| | | |
|---|---|---|
| Composition of fish meal | protein | 72.5% |
| | fat | 8.7% |
| | ash | 11.8% |
| | water | 8.5% |
| Water content after drying | meal + water | 3.3% |
| | meal + sodium caseinate + water + transglutaminase | 3.6% |
| Wear test, remaining pellets | meal + water | 1.2% |
| | meal + sodium caseinate + water + transglutaminase | 86.3% |

The example shows that blending around 125 ppm transglutaminase into a mixture of fish meal, sodium caseinate and water produced pellets with considerably greater firmness and strength than pellets formed from a feed mass (fish meal+water) without this enzyme additive.

The enzyme transglutaminase in powder form can be blended with one or more of the other dry ingredients of the feed before water is added in the form of liquid, for example pure water, stickwater, stickwater concentrate, other protein-enriched liquid or water vapour.

Drying may take place immediately after forming into pellets, as long as care is taken to ensure that the temperature does not rise above 60° C., thus giving the enzyme sufficient time to act to create a protein matrix before the water activity becomes so low that the enzyme will no longer act as a catalyst.

Transglutaminase produced by temperature-tolerant bacteria will be able to act at temperatures higher than 60° C.

Production conditions can thus be above 60° C. if thermostable transglutaminase is employed.

EXAMPLE 2

In this case another source of protein (soya) was used, whose real protein level is about 20% lower than that of fish meal. The feedstuff was prepared largely as indicated in Example 1.

500 g soya meal (Hamlet) and 700 ml water were mixed to the formation of a dough, which was formed into pellets and dried for about 40 minutes. As in example 1, a wear test was carried out. After the test had been completed, the remaining whole pellets were subjected to a new wear test, this time with four metal balls and at 150 revolutions. 25 g transglutaminase product containing 125 mg transglutaminase and 15 g sodium caseinate was stirred into 700 ml water at about 40° C. The solution was added to 500 g soya meal flour, blended and formed as indicated in example 1, incubated at 40° C. for 60 minutes and dried for about 60 minutes.

Result

| | | |
|---|---|---|
| Composition of soya meal | protein | 56.5% |
| | fat | 1.0% |
| | ash | 7.1% |
| | water | 7.9% |
| Water content after drying | meal + water | 10.0% |
| | meal + sodium caseinate + water + transglutaminase | 7.2% |
| Wear test without balls, remaining pellets | meal + water | 85.6% |
| | meal + sodium caseinate + water + transglutaminase | 95.8% |
| Wear test without balls, remaining pellets | meal + water | 35.5% |
| | meal + sodium caseinate + water + transglutaminase | 72.0% |

The invention also comprises other enzymes that catalyse the formation of covalent bonds between amino acids that form part of the protein chains in the raw materials of the protein in the feed.

Such an enzyme can, for example, catalyse an equivalent reaction between asparagine and lysine (å-(β-aspartyl) lysine bond) (transasparaginase).

Other examples are the enzyme protein disulphide isomerase (EC 5.3.4.1), which catalyses the rearrangement of cystine and the enzyme lipoxygenase.

A method for making feed for carnivorous animals, especially feed for farmed fish, including modifying protein structure of pre-shaped feed pellets, spheres, and similar feed particles or pieces, in order to achieve shape permanence, strength and firmness of said feed pellets and the like, wherein said properties are maintained subsequent to a possible incubation, drying, further processing, storage and transport, and wherein is used a catalyzing enzyme such transglutaminase, characterized in that said enzyme catalyzing the formation of covalent bonds between amino acids included in the protein chains of the protein raw material containing proteins in native or denatured form and that, to a substantial degree, constitutes structureless processed raw materials such as stickwater, stickwater concentrate, and structureless dry processed raw materials (powders) such as fish meal, blood meal, feather meal, or bone meal, wheat gluten, maize gluten, soy meal, canola meal, casein, sodium caseinate, gelatin or collagen, is mixed to the ready-mixed feed mass or, alternatively, to one or more of its ingredients prior to mixing, in order to build a protein network of said structureless raw materials, whereupon the feed mass to which the catalyst is added in the form of said enzyme is formed into feed pellets or the like. Alternatively, that said enzyme is applied to the surface of pre-shaped feed pellets, which are incubated at a temperature and for a period adjusted according to the kinetic properties of the enzyme, such that covalent bonds are established between said amino acids, and that said feed pellets or the like are further processed, conservation being effected through drying, and that, subsequent to the pellet shaping process, a reaction temperature is established in the range of 0–60° C., preferably 10–50° C., and wherein pre-shaped feed pellets, spheres and similar feed particles exhibit the desired shape performance, said protein network having been built up in such a way that it does not only form gel, but such that increased mechanical strength is established and maintained subsequent to the drying.

The method further wherein a catalyzing enzyme is used, such as transglutaminase, transasparaginase, protein disulphide isomerase and/or lipoxygenase, characterized in that said enzyme(s) is (are) added to the feed mass in an amount corresponding to at least 10 ppm of the (dry) weight of the feed mass and that, subsequent to the pellet shaping process, the reaction temperature is established in the range of 0–60° C., preferably 10–50° C., (does not apply for thermostabile transglutaminase that may function as a catalyst at temperatures greater than 60° C.), whereupon feed pellets are incubated and dried (e.g. in 60 and 50 minutes, respectively, dependent upon the temperature), so that the catalyzing property of the enzyme ceases when said feed pellets are pre-dried.

The method further characterized in that the enzyme transglutaminase are added in powder form to dry feed mass or, alternatively, to one or more of its ingredients prior to mixing, the transglutaminase powder being mixed into the same at the stage prior to the mixture of water into the mixture in the form of a liquid, such as pure water, stickwater, stickwater concentrate, other protein containing liquid and/or water vapor.

The method further characterized in that to a blending liquid for the feed mass (which has approximately the same weight as the last-mentioned) is added about 20 ppm or more transglutaminase, referred to the weight of the blending liquid, said transglutaminase being stirred and agitated into the blending liquid to form thereon an aqueous solution or suspension, the solution or suspension being mixed with a dry feed mass of approximately the same weight as the blending liquid.

The method further characterized in that the enzyme transglutaminase, is in a condition wherein it is dissolved in vapor, forming a solution, suspension or washing in a suitable liquid, such as water, is applied to the surface of pre-shaped feed pellets and that, subsequently, to the pellet shaping process, a reaction temperature is established within the range of 0–60° C., preferably 10–50° C., (not including thermostabile transglutaminase which may function as a catalyst at temperatures greater than 60° C.), whereupon feed pellets are incubated and dried (e.g. for 60 and 50 minutes, respectively, dependent upon the temperature), so that the catalyzing property enzyme ceases when said feed pellets are pre-dried.

A feed mass intended for the formation of feed particles (pellets), for carnivorous animals, especially farmed fish, prepared, made and processed in accordance with the method as set forth in any of the preceding disclosure, and where any catalyzing enzyme, particularly transglutaminase, has been added to said feed mass, characterized in that said catalyzing enzyme, such as transglutaminase, within said feed mass has catalyzed a reaction between amino acids, especially glutamine and lysine, included in the protein chains of the protein raw material of the feed mass, said raw material containing proteins and native or denatured form and which, to a substantial degree, constitutes structureless processed raw materials, such as stickwater, stickwater concentrate, and structureless dry processed raw materials (powders), such as fish meal, blood meal, feather meal or bone meal, wheat gluten, maize gluten, soya meal, canola meal, casein, sodium caseinate, gelatin, or collagen.

The feed mass further characterized in that the feed mass also contains micronutrients.

The feed mass further characterized in that the feed mass is conserved exclusively through drying.

The use of enzyme transglutaminase as a catalyst for a protein and amino acid containing feed mass to be shaped into pellets for farm fish, with the purpose of catalyzing a reaction resulting in the formation of covalent bonds between amino acids included in the protein chains of the raw materials of said feed mass, and said raw materials thereof containing proteins in native or denatured form."

What is claimed is:

1. A feed for carnivorous animals comprising:
  A. a protein raw material having a protein structure and a catalyzing enzyme, said catalyzing enzyme forming covalent bonds between amino acids of proteins of the protein raw material, the protein raw material comprising proteins in denatured form, the protein raw material comprising structureless processed raw materials being selected from the group consisting of stickwater, stickwater concentrate, and structureless dry processed raw materials in the form of powders, or any combination thereof, said powders being selected from the group consisting of fish meal, blood meal, feather meal, bone meal, wheat gluten, maize gluten, soy meal, canola meal, casein, sodium caseinate, gelatin, and collagen or any combination thereof, said catalyzing enzyme building a protein network for said structureless processed raw materials, wherein said protein raw material and said catalyzing enzyme are shaped into consumable feed pellets having shape permanence, strength, and firmness, said consumable feed pellets having a water content equal to or less than 20%.

2. The feed according to claim 1, wherein said catalyzing enzyme is selected from the group consisting of transglutaminase, transasparaginase, protein disulfide isomerase and lipoxygenase, or any combination thereof, said catalyzing enzyme comprising an amount of approximately at least 10 parts per million of the weight of the protein raw material.

3. The feed according to claim 2, wherein said catalyzing enzyme is transglutaminase, said transglutaminase comprising powder transglutaminase, wherein said powder transglutaminase is combined to said protein raw material.

4. A feed for carnivorous animals comprising:
  A. a raw protein material, said raw protein material having protein structure, said protein structure comprising protein chains and protein in a denatured form, said protein chains having covalent bonds and amino acids, said raw protein material being structureless processed raw material selected from the group consisting of stickwater, stickwater concentrate, fish meal, blood meal, feather meal, bone meal, wheat gluten, maize gluten, soy meal, canola meal, casein, sodium caseinate, gelatin, and collagen and any combination thereof;
  B. a catalyzing enzyme, said enzyme comprising transglutaminase, said catalyzing enzyme catalyzing the formation of covalent bonds between said amino acids, wherein said raw protein material and said catalyzing enzyme are formed into consumable feed pellets having enhanced shape permanence, strength, and firmness.

5. The feed according to claim 4, wherein said catalyzing enzyme is selected from the group consisting of transglutaminase, transasparaginase, protein disulfide isomerase, lipoxygenase, and any combination thereof, and further said catalyzing enzyme comprising an amount of at least 10 parts per million as compared to the dry weight of the feed.

6. The feed according to claim 5, wherein said catalyzing enzyme is transglutaminase in a powder form wherein said powder transglutaminase is combined to said structureless processed raw materials, said feed further comprising a blending liquid, said blending liquid being selected from the group consisting of water, pure water, stickwater, stickwater concentrate, water vapor, and protein containing liquids or any combination thereof.

7. The feed according to claim 5, wherein said blending liquid has approximately the same weight as the raw protein materials and further wherein about 20 parts per million of transglutaminase is combined to said blending liquid.

8. The feed according to claim 4, wherein said transglutaminase is a solution.

9. The feed according to claim 4, wherein said consumable feed pellets are substantially ball-shaped.

* * * * *